(12) United States Patent
Buressiniani (10) Patent No.: US 9,072,503 B2
(45) Date of Patent: Jul. 7, 2015

(54) AUTOMATIC DEVICE FOR TRANSCUTANEOUS BIOPSY

(75) Inventor: Fabio Buressiniani, Rome (IT)

(73) Assignee: Odoardo Buressiniani (IT)

( * ) Notice: Subject to any disclaimer, the term of this patent is extended or adjusted under 35 U.S.C. 154(b) by 764 days.

(21) Appl. No.: 13/386,831

(22) PCT Filed: Jul. 27, 2010

(86) PCT No.: PCT/IB2010/053407
§ 371 (c)(1),
(2), (4) Date: Apr. 5, 2012

(87) PCT Pub. No.: WO2011/013066
PCT Pub. Date: Feb. 3, 2011

(65) Prior Publication Data
US 2012/0191007 A1    Jul. 26, 2012

(30) Foreign Application Priority Data

Jul. 27, 2009 (IT) .............................. RM2009A0392

(51) Int. Cl.
*A61B 10/02* (2006.01)

(52) U.S. Cl.
CPC ......... *A61B 10/0233* (2013.01); *A61B 10/0283* (2013.01); *A61B 2010/0208* (2013.01)

(58) Field of Classification Search
CPC .......................................... A61B 10/02–10/04
USPC .................................................. 600/566–568
See application file for complete search history.

(56) References Cited

U.S. PATENT DOCUMENTS

| | | | |
|---|---|---|---|
| 3,605,721 A | 9/1971 | Hallac | |
| 4,693,257 A | 9/1987 | Markham | |
| 5,573,008 A | 11/1996 | Robinson et al. | |
| 5,885,226 A * | 3/1999 | Rubinstein et al. | 600/564 |
| 6,015,391 A * | 1/2000 | Rishton et al. | 600/567 |
| 7,455,645 B2 * | 11/2008 | Goldenberg | 600/564 |
| 7,918,804 B2 * | 4/2011 | Monson et al. | 600/568 |
| 2005/0054947 A1* | 3/2005 | Goldenberg | 600/567 |
| 2005/0054948 A1* | 3/2005 | Goldenberg | 600/567 |
| 2006/0200040 A1 | 9/2006 | Weikel et al. | |
| 2007/0142743 A1* | 6/2007 | Provencher et al. | 600/562 |
| 2009/0227895 A1* | 9/2009 | Goldenberg | 600/567 |

FOREIGN PATENT DOCUMENTS

| | | |
|---|---|---|
| JP | 09192134 A | 7/1997 |
| JP | 2005052408 A | 3/2005 |
| JP | 2006506200 A | 2/2006 |
| JP | 2006239433 A | 9/2006 |

(Continued)

*Primary Examiner* — Sean Dougherty
*Assistant Examiner* — Michael C Stout
(74) *Attorney, Agent, or Firm* — Laubscher, Spendlove & Laubscher, P.C.

(57) ABSTRACT

A device for transcutaneous biopsy includes a casing consisting of a first half shell and a second half shell that are fixable to one another. Inside the casing there is defined a chamber into which slides a slide element to which a first cannula and a second cannula are connected. The second cannula is inserted inside the first cannula, both of them having a common longitudinal axis. The first cannula is provided with a locking element. The locking element, which is suitable for interacting with the second cannula, is provided with a pair of notches interacting with a pair of lamina elements with which the second cannula is provided.

20 Claims, 8 Drawing Sheets

(56) References Cited

FOREIGN PATENT DOCUMENTS

| WO | 9624289 | A2 | 8/1996 |
| WO | 01/22887 | A1 | 4/2001 |
| WO | 2004045417 | A1 | 6/2004 |
| WO | 2005013831 | A2 | 2/2005 |
| WO | 2008122870 | A1 | 10/2008 |

\* cited by examiner

AUTOMATIC DEVICE FOR TRANSCUTANEOUS BIOPSY

This application is a §371 National Phase entry of PCT International Application No. PCT/IB2010/053407 filed Jul. 27, 2010. PCT/IB2010/053407 claims priority to IT Application No. RM2009A000392 filed Jul. 27, 2009. The entire contents of these applications are incorporated herein by reference.

The present invention relates to an automatic device for transcutaneous biopsy driven by a spring, pneumatic, hydraulic, electromechanical or electromagnetic driving system to take biopsy samples of soft and hard tissue for clinical examination.

Devices for transcutaneous biopsy are known that consist of a body made of plastics or metal, for example of aluminium or steel, and of slidable elements for housing a needle, for example slides or carriages, slidably driven, for example, by springs.

The needle substantially consists of a cannula that has a sharp distal end that is suitable for penetrating the tissues of the body of a patient to cut a distal part, and a mandrel that is insertable in the cannula and can slide inside the cannula. The mandrel is also sharp at a distal end thereof and is provided with a housing that extends in a longitudinal direction and is suitable for retaining a tissue sample to be cut.

In order to conduct the biopsy, the cannula of the needle is placed on a first slide or carriage of the biopsy device, the mandrel is placed on a second slide or carriage and is introduced into the respective cannula, positioning said first slide or carriage and said second slide or carriage such that the cannula covers the housing of the mandrel.

After the needle has been inserted into the body of a patient until the zone from which a tissue sample has to be removed, the device is driven to advance the second slide or carriage that drags with it the mandrel, that advances in turn, exiting from the cannula of the needle so as to uncover the housing into which a portion of tissue penetrates. At this point the first slide or carriage is advanced, such that the cannula advances on the mandrel, cutting from the rest of the tissue the portion of tissue that has penetrated into the housing and covering the housing.

One drawback of these devices for transcutaneous biopsy consists of the fact that the friction phenomena between the metal walls of the needle and the resistance of the tissue being cut, absorb a significant fraction of the propulsive force that the driving system applies to the slide or carriage that carries the cannula during the advancing step of the latter, with the consequence that during the releasing step the tissue is often not cut cleanly and totally or that, even worse, the system of needles does not shut.

Further devices for transcutaneous biopsy are further known that comprise a needle with a hollow cylindrical shape, of variable diameter and length, an end of which, so-called proximal end, is provided with a grip suitable for enabling the operator to use the needle, whilst the other end, so-called distal end, is provided with a cutting edge that is suitable for enable the tissue sample that is to be removed to be separated at least partially from the surrounding tissue.

The needle is generally coupled with a mandrel consisting of a steel rod of dimensions that are such as to be able to slide inside the needle. Said rod is provided with a sharpened end that protrudes from the distal end of the needle and is intended to perforate the tissues of the body of the patient until it reaches the zone from which a sample tissue has to be removed. After the needle with the mandrel inserted therein has reached the zone from which a tissue sample has to be removed, the mandrel is extracted and the needle is pushed further inside the tissue, such that a tissue sample penetrates inside the needle.

Such further devices further comprise elements to be slidably inserted through the proximal part of the needle, after the latter has been introduced into the body of the patient and has internally gathered a tissue sample to be taken.

Such locking elements are shaped in such a manner as to be able to be inserted between a zone of the internal wall of the needle and the tissue sample gathered therein.

When the locking element is pushed up to the tapered end of the hollow body, it is deflected radially inside so as to force the tissue sample against the opposite zone of the internal wall of the hollow needle.

This causes a certain locking force of the sample between a part of the locking element and the internal wall of the needle to be created.

This locking force during the step of extraction of the needle should maintain the tissue sample inside the needle, whilst the distal end of the sample is detached from the surrounding tissues both through the effect of the traction that is exerted to extract the needle and through rotations of the needle.

Nevertheless, also these further devices have significant drawbacks.

Inserting the locking element of the needle is a very delicate operation as it can often damage the sample that has penetrated into the distal end of the needle, by crushing or by scratching; the removed but damaged tissue can create falsifications during the clinical examination and the patient is thus forced to submit again to a biopsy with the consequent significant worsening of the trauma and suffering caused.

The locking force that is created through the effect of the friction between the sample, the locking element and the internal wall of the hollow needle may not be sufficient to clamp the sample. In this situations the effect of the rotations impressed on the needs may not have the hoped-for effect and it is thus impossible to take the sample.

Another negative condition that may occur owing to insufficient locking force is the loss of the sample from the internal cavity of the needle, during the extracting operation. In this situation it is possible to lose the sample inside the tissues that the hollow needle traverses before being removed.

The object of the present invention is to provide a device for transcutaneous biopsy that does not have the aforementioned drawbacks and enables the tissue samples to be taken in a reliable manner.

Owing to the invention, the influence of friction between the movable parts of the biopsy device is reduced and further a reliable separation of the tissue sample to be taken from the rest of the tissue is guaranteed without the risk of damage to the tissue sample.

One embodiment of the invention is disclosed below, by way of non limiting example, with reference to the attached drawings, in which.

Figure 1:
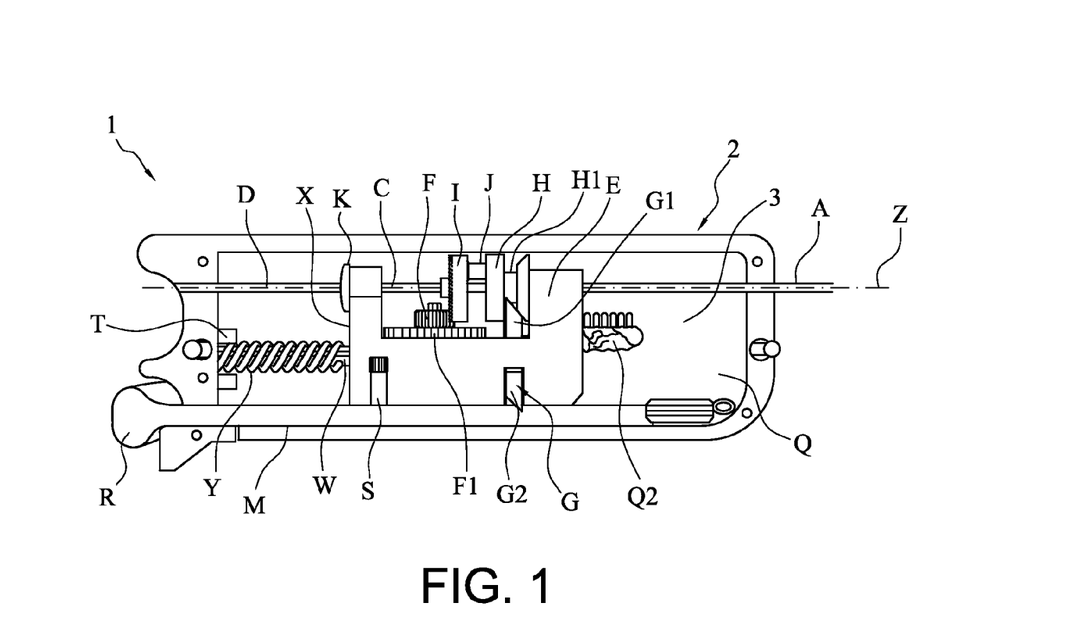
FIG. 1 is an elevation view of the inside of the device according to the invention.
Figure 2:
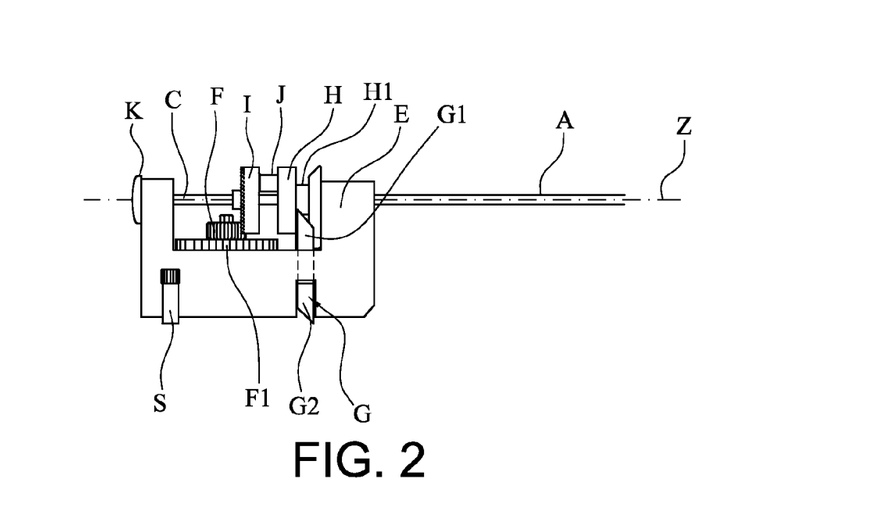
FIG. 2 is a detail of FIG. 1.
Figure 3:
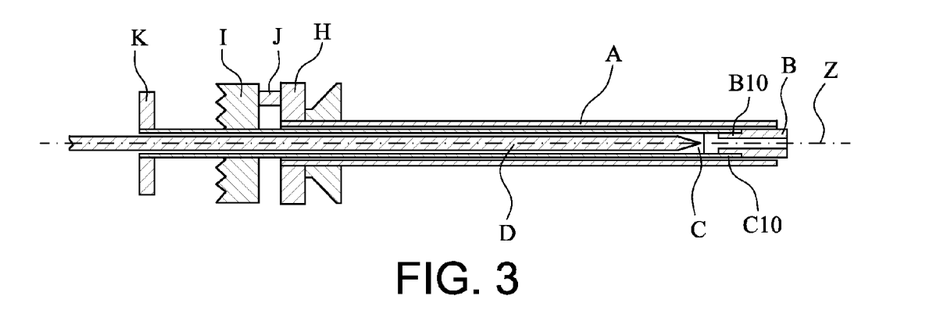
FIG. 3 is an enlarged and sectioned detail of FIG. 2, relating to a part of the device according to the invention in which an organic tissue sample is trapped and detached from the original tissue.
Figure 4:
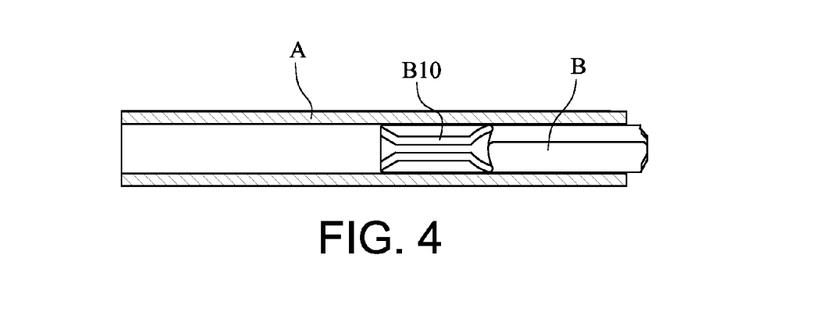
FIG. 4 is an enlarged detail of FIG. 3.
Figure 21:
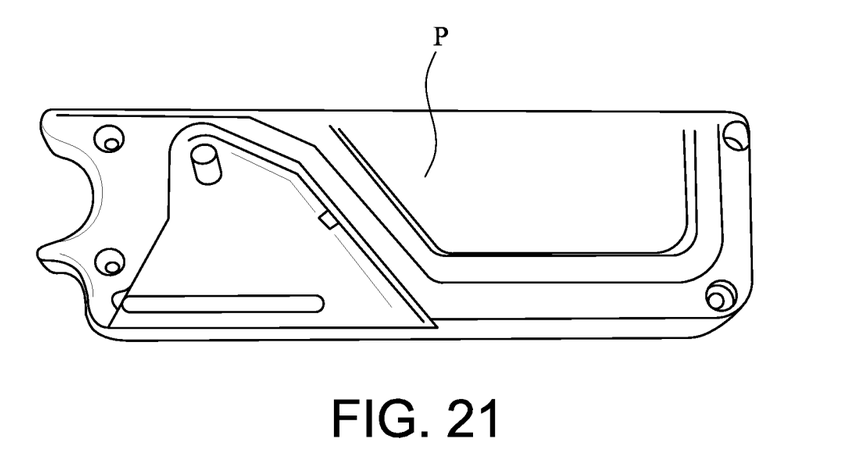
FIG. 21 is an outside view of a first half shell that constitutes the outside casing of the device according to the invention.
Figure 22:
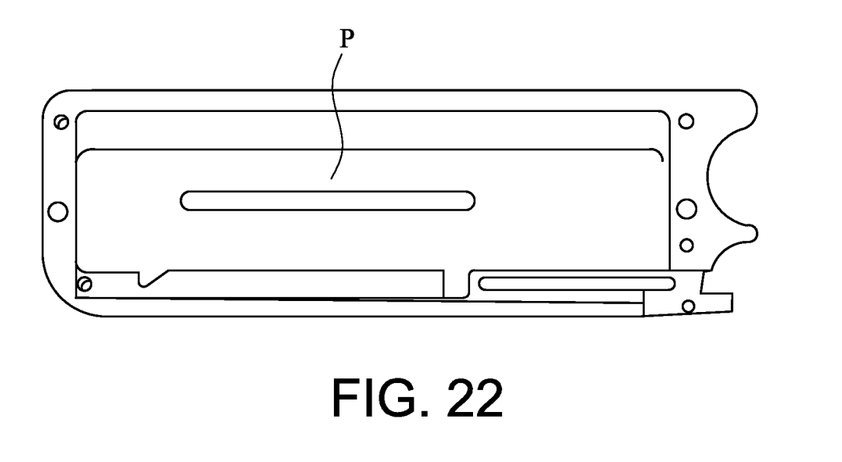
FIG. 22 is an inside view of the first half shell of FIG. 21.
Figure 23:
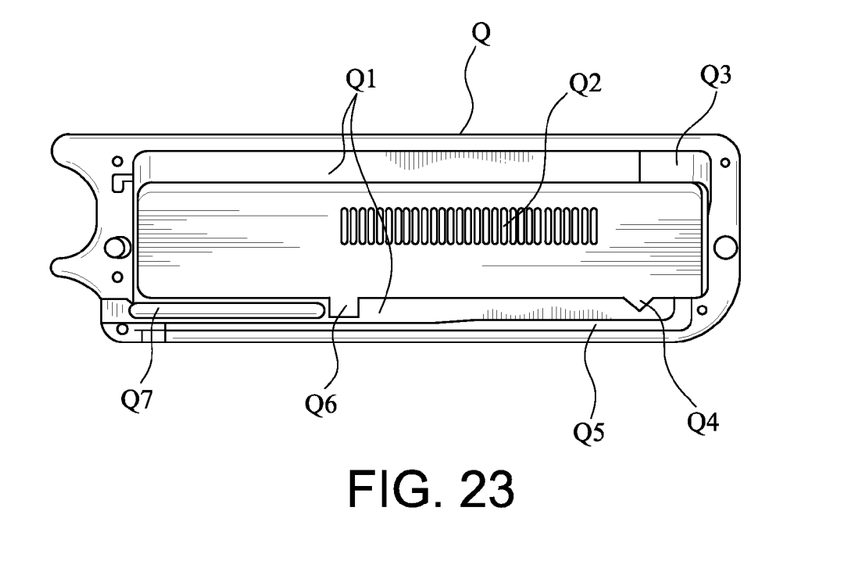
FIG. 23 is an outside view of a second half shell that constitutes the outside casing of the device according to the invention.
Figure 24:
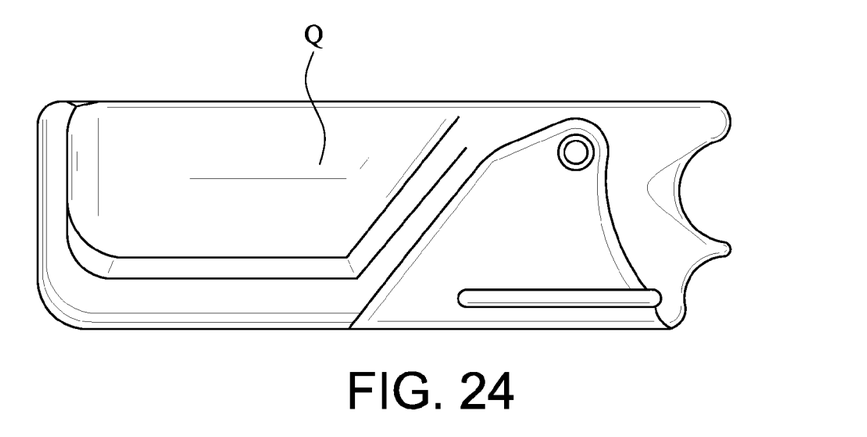
FIG. 24 a view of the inside of the second half shell in FIG. 23.

In FIG. 1 there is illustrated a device 1 according to the invention that comprises a casing 2 consisting of a first half shell P (FIG. 21) and of a second half shell Q that can be fixed together. In FIG. 1 only the second half shell Q is visible.

Inside the casing 2 there is defined a chamber 3 in which there is housed a slide element E that is slidable inside said chamber 3 along guides Q1. A first cannula A, consisting of a first hollow cylindrical body and a second cannula C consisting of a second hollow cylindrical body are connected to the slide element E. The second cannula C is inserted inside the first cannula A that can slide, at least to a limited extent, in relation to the second cannula C in the direction of a longitudinal axis Z that is common to both cannulas A and C and is parallel to the sliding direction of the slide element E inside the chamber 3.

A distal end of the first cannula A protrudes from the casing 2 with a minimum protrusion of set value that is suitable for enabling said distal end to be inserted into the body of the patient until it reaches a zone from which a sample of tissue can be taken for a biopsy examination.

Figure 15:
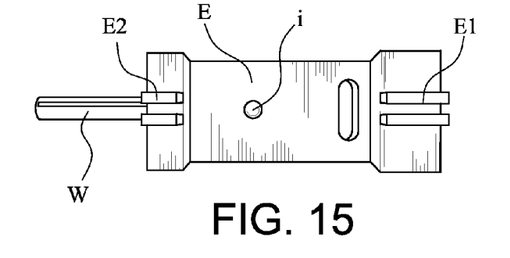
FIG. 15 is a top view of FIG. 13.
Figure 16:
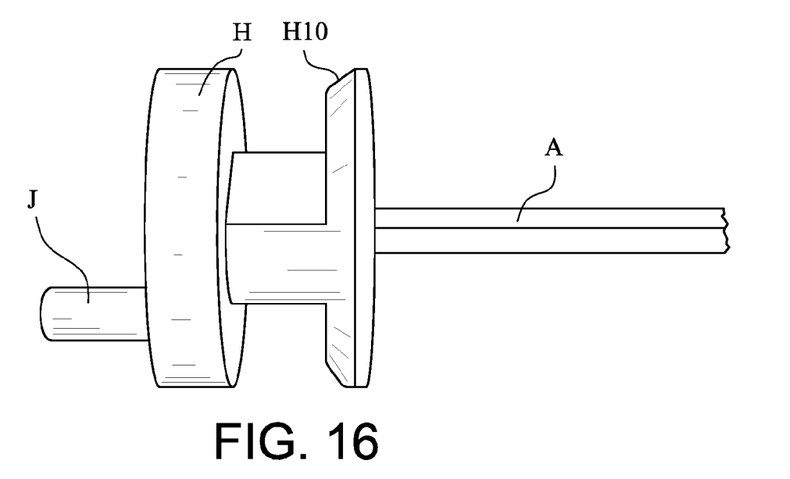
FIGS. 16, 17 and 18, are enlarged details of FIG. 13.
Figure 17:
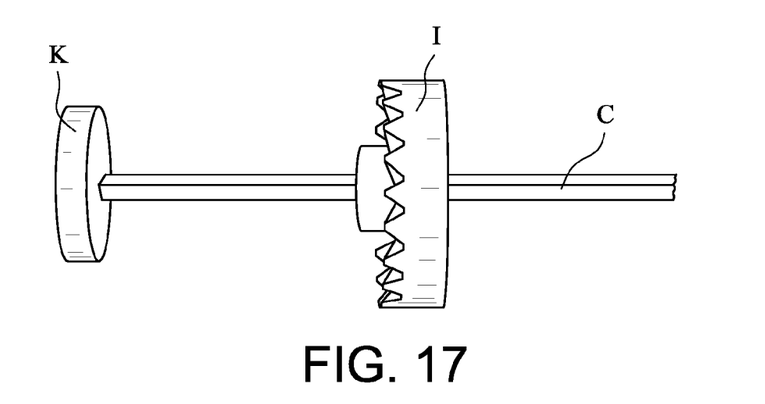
Figure 18:
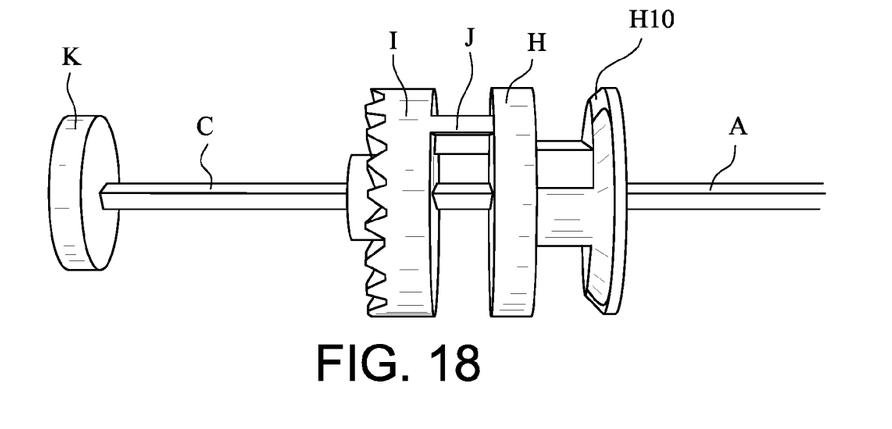

The first cannula A and the second cannula C are connected to the slide element E such as to be able to rotate around said longitudinal axis Z. The first cannula A and the slide element E are connected by inserting the first cannula A into a first seat E1 (FIG. 15) in which the first cannula A is free to rotate around the longitudinal axis Z. Similarly, the second cannula C and the slide element E are connected by inserting the second cannula C into a second seat E2 (FIG. 15) in which the second cannula C is free to rotate around the longitudinal axis Z.

The second cannula C is further provided, at a proximal end thereof, with a fixing element K that prevents the second cannula C from sliding with respect to the slide element E in a direction parallel to said longitudinal axis Z.

The second cannula C terminates, at a distal end thereof with a pair of diametrically opposite lamina elements C10.

To the distal end of the first cannula A, inside the first cannula A, a locking element B is fixed that is intended for interacting with the lamina elements C10 of the second cannula C to avoid deformation of the lamina elements C10 when they come into contact with the organic tissue and to deflect the lamina elements C10 to the longitudinal axis Z, as will be explained in greater detail below.

The locking element B consists of a third hollow cylindrical body (FIG. 5) that has, at a proximal end thereof, a pair of notches B10, that are diametrically opposite one another, suitable for receiving the lamina elements C10.

Figure 5:
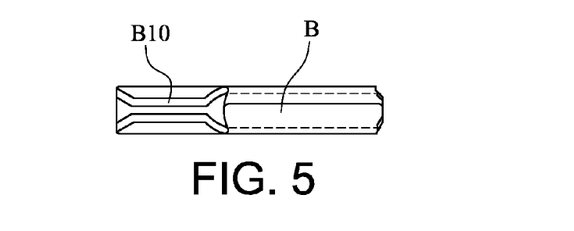
FIG. 5 is a detail of FIG. 4.
Figure 6:
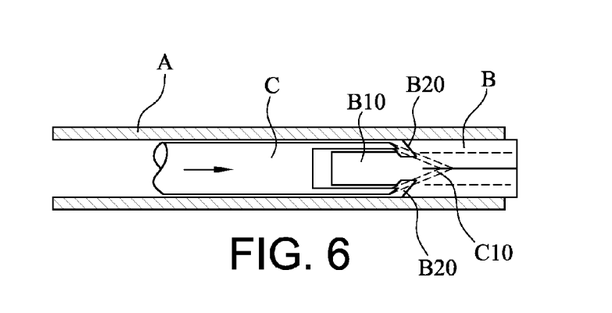
FIGS. 6 and 7 show a further enlarged detail of FIG. 3, in two different operating conditions.
Figure 7:
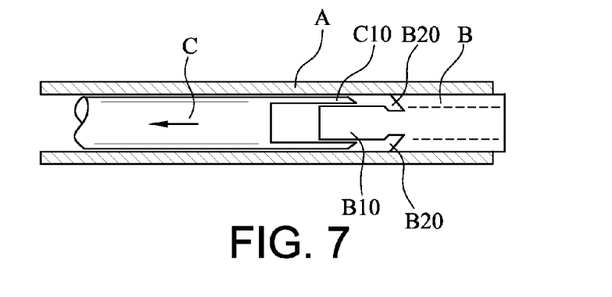
Figure 8:
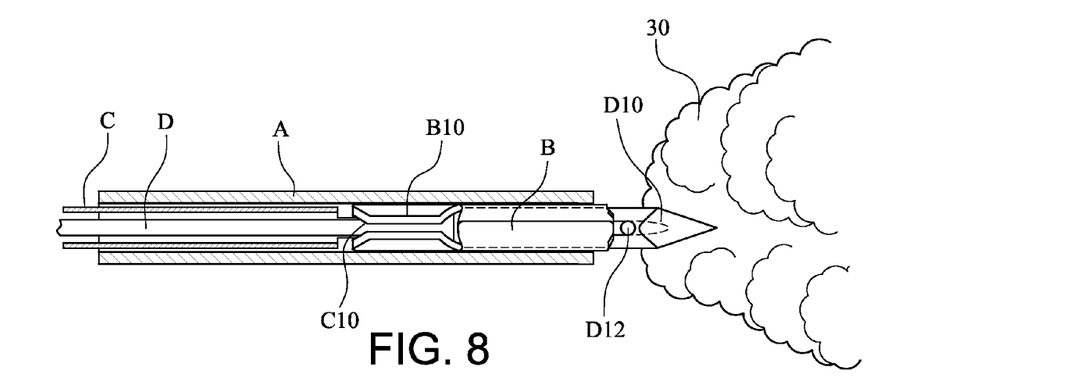
FIGS. 8, 9 and 10 illustrate the operation of the device according to the invention during removal of an organic tissue sample.

The notches B10 terminate at a distal end thereof against the wall of the third cylindrical body of the locking element B, in a zone in which said wall has a pair of diametrically opposite bevels B20, intended for interacting with the lamina elements C10 to deflect the lamina elements C10 to said longitudinal axis Z.

The first cannula A is fixed, at a proximal end thereof, to a first driving element H suitable for rotating the first cannula A around said longitudinal axis Z.

The first driving element H is connected by a connecting element J to a second driving element I splined on the second cannula C and consisting of a crown gear. The connecting element J is coupled with the first driving element H in such a manner that the first driving element H can slide on the connecting element J in a direction parallel to said longitudinal axis Z. The connecting element J can consist of a pivot having a first end fixed stiffly to the second driving element I, whilst a second end is slidingly coupled with the first driving element H, in such a manner that the first driving element H and the second driving element I are fastened together with respect to rotation but not with respect to translation in a direction parallel to the longitudinal axis Z. Consequently, also the first cannula A and the second cannula C are fastened together with respect to rotation but not with respect to translation in a direction parallel to the longitudinal axis Z.

A further locking element G that is slidable with respect to the slide element E in a direction that is substantially perpendicular to said longitudinal axis Z is associated with the slide element E. A first end G1 of the further locking element G is insertible into a throat H1 of the first driving element H whilst a second end G2 of the further locking element G is insertible into a seat Q4 of the second shell Q. The first end G1 and the second end G2 of the further locking element G are inclined with respect to the sliding direction of the further locking element G.

When the first end G1 of the further locking element G is inserted into said throat H1, the first driving element H is connected to the slide element E and the first cannula A cannot slide with respect to the second cannula C. Vice versa, when the locking element G reaches said seat Q4, the second end G2 thereof is inserted into said seat Q4, whilst the first end G1 exits the throat H1 in such a manner that the first driving element H is disconnected from the slide element E and the first cannula A can slide with respect to the second cannula C.

Inside the second shell Q an abutment Q3 is obtained against which the first driving element H comes into contact when the further locking element G reaches said seat Q4.

The crown gear I engages with a pinion F mounted free to rotate on an axis of rotation i fixed to the slide element E and perpendicular to said longitudinal axis Z. The pinion F is fixed to a gear wheel F1, which is also free to rotate on the same rotation axis i. The gear wheel F1 engages with a rack Q2 fixed inside the second half shell Q and arranged parallel to the direction on said longitudinal axis Z.

When the slide element E slides inside the chamber 3, the gear wheel F1, by engaging with the rack Q2 rotates around the rotation axis I. The pinion F transmits rotation motion to the crown gear I, which rotates, by the connecting element J, the first driving element H. In this manner the first cannula A, fixed to the driving element H, and the second cannula C, fixed to the crown gear I are rotated together at the same speed around the common axis Z thereof during sliding of the slide element and inside the chamber 3. The simultaneous rotation of the first cannula A and of the second cannula C means that friction resistance cannot develop between the two cannulas during rotation thereof, which increases efficiency of the biopsy device according to the invention.

The slide element E is provided, on an end side X thereof, with a rod W that protrudes from said end side X and is parallel to the sliding direction of the slide element E. On the rod W an elastic element Y, for example a coil spring, is placed, an end of which is received in a seat T obtained in the second half shell Q.

The coil spring provides the propulsion force for sliding the slide element E in the chamber 3.

In fact, by making the slide element E move back toward said seat T, i.e. to the left with reference to FIG. 1, the coil spring Y is compressed, accumulating elastic energy that, when it is released, generates a thrust force that slides the slide element E away from said seat T, i.e. to the right, with reference to FIG. 1.

The sliding of the slide element E toward said seat T, to load the coil spring Y, is controlled by a traction element M that is slidable in the lower part of the second shell Q along a guide Q5 and is provided with a grip R that protrudes outside the casing 2 of the device.

Figure 19:
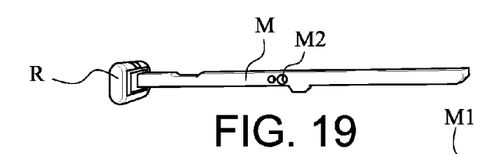
FIG. 19 illustrates an enlarged detail of FIG. 1.
Figure 20:
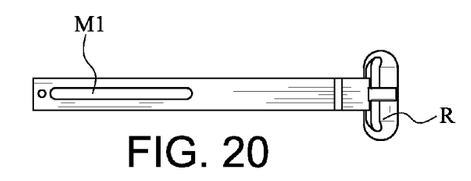
FIG. 20 is a top view of the detail in FIG. 19.

The traction element M (FIGS. 19 and 20) is provided with a slot M1, into which a lower end i1 of the axis i is inserted. By exerting traction on the traction element M, so as to make the traction element M exit the casing 2, when said lower end i1 comes into contact with an end of the slot M1, the slide element E is dragged toward the seat T of the coil spring Y and the latter is loaded. In addition to the grip R, the traction element M can be provided with a transverse moving pivot M2, an end of which protrudes through a further slot Q7 of the second half shell Q and enables the traction element M to be driven by using the transverse pivot M2 instead of the grip R.

In order to maintain the slide element E in the position in which the traction spring Y is loaded, an arresting element S is provided, for example a stop pawl, that is inserted into a third seat E4 of the slide element E and can be engaged in a further seat Q6 obtained in the second shell Q to lock the slide element E is position.

Figure 12:
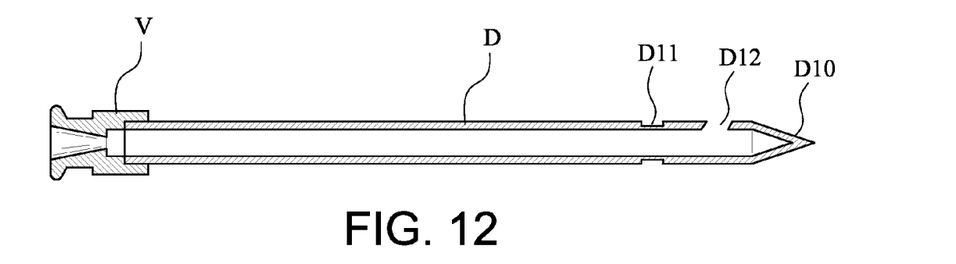
FIG. 12 is an axial section of the device in FIG. 11.
Figure 13:
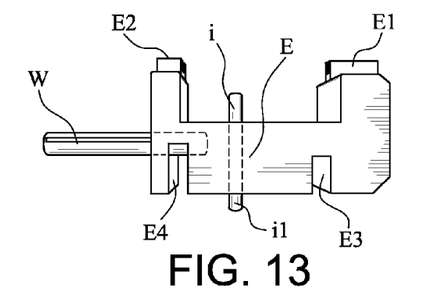
FIG. 13 illustrates a detail of FIG. 2.
Figure 14:
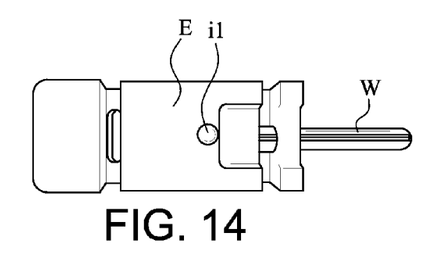
FIG. 14 is a bottom view of FIG. 13.

The biopsy device according to the invention further comprises a mandrel D (FIG. 12) that is fixed to the casing and is insertable inside the second cannula C and the locking element B until a penetration tip D10 is made to emerge from a distal end of the latter, the penetration tip D10 being used to facilitate the introduction of the cannulas A and C into the tissues of the body of a patient.

The spindle D is internally hollow and is provided, at a distal end thereof, with a connecting element V, for example a Luer cone, by means of which the spindle D can be connected to a sucking device to create a vacuum inside the spindle D. The vacuum is used, for example, to suck organic liquids inside the spindle for cytological examinations. Said organic liquids are sucked through an opening D12 made near the tip D10.

The spindle D is further provided with a throat D11 in which a seal ring can be inserted that is suitable for ensuring that the spindle D can slide in a sealed manner inside the second cannula C.

The operation of the biopsy device according to the invention is disclosed below.

After the device according to the invention has been assembled by connecting the cannulas A and C on the slide element E and inserting said cannulas on the spindle D, the spring Y is loaded, by acting on the traction element M so as to make the slide element E move back toward the end of the chamber 3 where the seat T is located into which is inserted an end of the spring Y, and, after loading the spring Y, the slide element E is locked in position by the pawl S. In this position of the slide E, the penetration tip D10 of the spindle D protrudes from the distal end of the cannula A and is usable to facilitate penetration of the distal end of the first cannula A into the body of a patient, until it reaches a zone from which a tissue sample has to be removed for a biopsy examination.

After inserting, with the help of the spindle D, the distal end of the cannula A into the body of a patient and after reaching with said distal end the zone from which a tissue sample has to be taken, a sample of organic liquid can be taken for a possible cytological examination, connecting the connecting element V to a sucking device.

Figure 9:
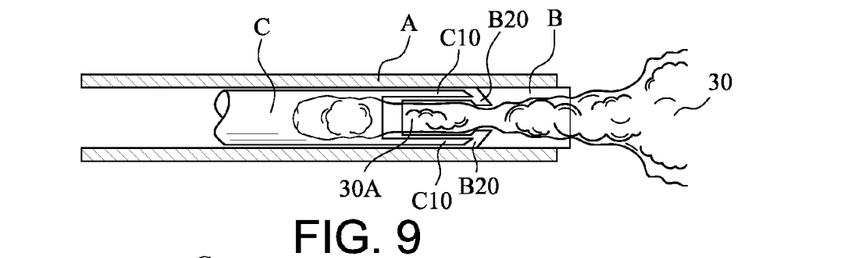
Figure 10:
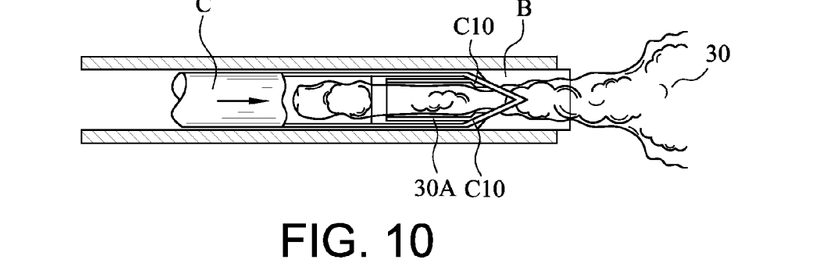
Figure 11:
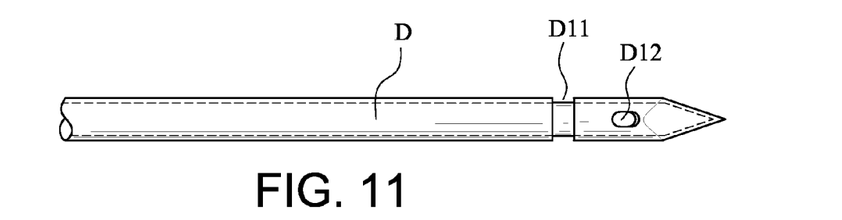
FIG. 11 illustrates a further detail of the device according to the invention.

In order to take a tissue sample, the slide element E is freed, acting on the arresting element S in such a manner that the compressed spring Y pushes the slide element E forwards. During the advance of the slide element E, the first cannula A and the second cannula C advance with respect to the spindle D, which thus withdraws with respect to the first cannula A and to the second cannula C such that a portion 30A of organic tissue 30 can penetrate the locking element B fixed to the distal end of the first cannula A, until it reaches the proximal end of the locking element B, in which the notches B10 are made inside which the lamina elements C10 of the distal end of the second cannula C (FIG. 9) are inserted. During the advance of the slide element E, the first cannula A and the second cannula C are rotated by the gear wheel F1, which engages with the rack Q2, the pinion F, the crown gear I and the first driving element H. When the first driving element H comes into contact with the abutment Q3, the end G2 of the further locking element G is at the seat Q4 of the second half shell Q and thus slides downwards, disengaging from the first driving element H. In this manner the first driving element H is disconnected from the slide element E, such that the slide element E can advance further, through the effect of the thrust of the spring Y, whilst the first driving element H, with the first cannula A connected thereto, remains stationary against the abutment Q3.

A further advance of the slide element E advances the second cannula C with respect to the first cannula A and the lamina elements C10 are pushed against the pair of bevels B20 of the locking element B and are deflected towards the longitudinal axis Z of the second cannula C, until it closes the cannula space completely, entrapping said portion of organic tissue 30A therein. The rotation motion of the second cannula C is such that the lamina elements C10 can separate without tearing, with a cutting action, the portion of organic tissue 30A from the rest of the organic tissue 30, without risk of damaging said portion of tissue 30A.

After the slide element E has reached the end of the stroke and a portion of organic tissue 30A has remained trapped in the second cannula C, the slide element E is made to move back by acting on the traction element M. Whilst the slide element E moves back, the further locking element G, through the effect of the interaction of the second end G2 with the walls of the seat Q4, moves upwards until the first end G1 thereof is inserted into the throat H1 of the first driving element H, again fastening the first driving element H and making the first cannula A advance with respect to the second cannula C, such that the lamina elements C10 move away from the bevels B20 and return to a position that is parallel to the longitudinal axis Z, freeing the space of the cannula C. Whilst the slide element E moves back, the first cannula A and the second cannula C slide on the spindle D, the tip D10 of which pushes the tissue sample 30A outside the distal ends of the first cannula A and of the second cannula C, in such a manner that the tissue sample 30A can easily be recovered. Owing to the invention, taking an organic tissue sample is made easy and secure, without there being substantially the risk of damage to the organic tissue sample during the sample-taking, owing to the fact that the organic tissue sample is separated from the rest of the tissue with a cutting action rather than with a tearing action, as occurs in the devices known from the prior art.

Further, owing to the fact that there is a relative motion of minimum amount between the first cannula A and the second cannula C, only in the final advancing step of the slide element E, the friction that develops during the drive of the device making optimum exploitation of the elastic energy of the spring Y possible, which substantially eliminates the risk of failure of the taking of the tissue sample due to insufficient thrust of the spring Y, which would make the entry of the tissue sample into the first cannula A and into the second cannula C problematic.

The invention claimed is:

1. A device for transcutaneous biopsy, comprising a casing including a first half shell and a second half shell that are fixable to one another, said casing defining a chamber into which a slide element is slidable in a sliding direction, wherein to said slide element there are connected a first cannula, including a first hollow cylindrical body, and a second cannula including a second hollow cylindrical body, said first cannula and said second cannula having a common longitudinal axis parallel to said sliding direction, said second cannula being inserted inside said first cannula, said first cannula being provided, at a distal end thereof, with a locking element suitable for interacting with said second cannula, said locking element comprising a third hollow cylindrical body fixed to the inside of said distal end of the first cannula, said third hollow cylindrical body being provided at a proximal end with a pair of notches, said second cannula being provided at a distal end thereof with a pair of lamina elements that are diametrically opposite one another and are suitable for interacting with said pair of notches, said notches terminating at a distal end thereof against a wall of said third cylindrical body in a zone in which said wall has a pair of diametrically opposite bevels intended for interacting with said lamina elements to deflect the lamina elements toward a longitudinal axis that is common to said second cannula and said first cannula.

2. A device according to claim 1, wherein said first cannula is insertable into a first seat of said slide element so as to be free to rotate with respect to said slide element and said second cannula is insertable into a second seat of said slide element so as to be free to rotate with respect to said slide element, said second cannula being provided at a proximal end thereof with a fixing element that prevents said second cannula from sliding with respect to said slide element in a direction parallel to said longitudinal axis.

3. A device according to claim 1, wherein a proximal end of said first cannula is fixed to a first driving element suitable for rotating said first cannula around said longitudinal axis.

4. A device according to claim 3, wherein said first driving element is connected by a connecting element to a second driving element splined on said second cannula.

5. A device according to claim 4, wherein said connecting element is coupled with said first driving element in such a manner that the first driving element can slide on the connecting element in a direction parallel to said longitudinal axis.

6. A device according to claim 4, wherein said second driving element comprises a crown gear that engages with a pinion mounted free to rotate on an axis fixed to the slide element and perpendicular to said longitudinal axis, said pinion being fixed to a gear wheel which is also free to rotate on said rotation axis, said gear wheel engaging with a rack fixed inside said second half shell and arranged parallel to said longitudinal axis.

7. A device according to claim 3, and further comprising a second locking element that is slidable with respect to said slide element in a direction that is perpendicular with respect to said longitudinal axis, said second locking element having a first end that is insertable into a throat of said first driving element.

8. A device according to claim 7, wherein a second end of said second locking element is insertable into a seat obtained in said second half shell.

9. A device according to claim 8, wherein said first end and said second end of said second locking element are inclined with respect to said direction perpendicular to said longitudinal axis.

10. A device according to claim 1, wherein an end side of said slide element is provided with a rod protruding from said end side in a direction parallel to said longitudinal axis and an elastic element placed on said rod, an end of said elastic element being received in a seat obtained in said second half shell.

11. A device according to claim 10, wherein said elastic element is a coil spring.

12. A device according to claim 11, and further comprising a traction element that is slidable in a lower part of said second half shell, said traction element being provided with a slit that is suitable for receiving a lower end of a rotation axis.

13. A device according to claim 12, wherein said traction element is provided at a proximal end thereof with a grip that protrudes outside said casing, said traction element including a transverse moving pivot having an end which protrudes outside said casing through a slot of said second half shell.

14. A device according to claim 1, wherein said slide element is provided with an arresting element inserted into a third seat of said slide element and suitable for engaging in a further seat of said second half shell for locking the sliding of said slide element.

15. A device for transcutaneous biopsy, comprising a casing including a first half shell and a second half shell that are fixable to one another and a spindle fixed to said casing, said casing defining a chamber into which a slide element is slidable in a sliding direction, wherein to said slide element there are connected a first cannula, including a first hollow cylindrical body, and a second cannula including a second hollow cylindrical body, said first cannula and said second cannula having a common longitudinal axis parallel to said sliding direction, said second cannula being inserted inside said first cannula, said first cannula being provided, at a distal end thereof, with a locking element suitable for interacting with said second cannula, said locking element comprising a third hollow cylindrical body fixed to the inside of said distal end of the first cannula, said third hollow cylindrical body being provided at a proximal end with a pair of notches, said second cannula being provided at a distal end thereof with a pair of lamina elements that are diametrically opposite one another and are suitable for interacting with said pair of notches, said spindle being coupled with said first cannula and to said second cannula such that said first cannula and said second cannula can slide on said spindle.

16. A device according to claim 15, wherein said spindle is provided with a penetration tip and is internally hollow.

17. A device according to claim 15, wherein a proximal end of said spindle is provided with a connecting element for connecting said spindle with a suction device to create a vacuum inside said spindle.

18. A device according to claim 16, wherein said spindle is provided with an opening adjacent to said penetration tip.

19. A device according to claim 15, wherein said spindle is provided with a throat into which a seal washer is insertable.

20. A device according to claim 3, wherein said second half shell is provided with an abutting element suitable for interacting with said first driving element for locking motion of said first driving element in a direction parallel to said longitudinal axis.

* * * * *